(12) United States Patent
Hu et al.

(10) Patent No.: US 9,474,477 B2
(45) Date of Patent: Oct. 25, 2016

(54) DIGITAL PULSE OXIMETER WITH AUTOMATIC DIRECTION-CHANGING FUNCTION

(71) Applicant: CONTEC MEDICAL SYSTEMS CO., LTD., Qinhuangdao (CN)

(72) Inventors: Kun Hu, Qinhuangdao (CN); Yunlong Xu, Qinhuangdao (CN); Jinling Zhang, Qinhuangdao (CN); Yatao Zhao, Qinhuangdao (CN); Zhichao Song, Qinhuangdao (CN)

(73) Assignee: CONTEC MEDICAL SYSTEMS CO., LTD., Qinhuangdao (CN)

( * ) Notice: Subject to any disclaimer, the term of this patent is extended or adjusted under 35 U.S.C. 154(b) by 885 days.

(21) Appl. No.: 13/625,805

(22) Filed: Sep. 24, 2012

(65) Prior Publication Data
US 2014/0088387 A1 Mar. 27, 2014

(51) Int. Cl.
*A61B 5/1455* (2006.01)
*A61B 5/00* (2006.01)
*A61B 5/11* (2006.01)

(52) U.S. Cl.
CPC .............. *A61B 5/14552* (2013.01); *A61B 5/11* (2013.01); *A61B 5/6826* (2013.01); *A61B 5/742* (2013.01)

(58) Field of Classification Search
CPC .............. A61B 5/1455; A61B 5/14551; A61B 5/14552; A61B 5/6826; A61B 5/72; A61B 5/743
See application file for complete search history.

(56) References Cited

U.S. PATENT DOCUMENTS

| | | | |
|---|---|---|---|
| 5,477,508 A * | 12/1995 | Will | G04G 21/00 368/189 |
| 5,490,523 A * | 2/1996 | Isaacson et al. | 600/323 |
| 6,584,336 B1 * | 6/2003 | Ali et al. | 600/323 |
| 6,654,621 B2 * | 11/2003 | Palatnik et al. | 600/322 |
| 8,185,179 B2 * | 5/2012 | Xu et al. | 600/323 |

FOREIGN PATENT DOCUMENTS

WO WO2008/019548 * 2/2008

* cited by examiner

*Primary Examiner* — Eric Winakur
(74) *Attorney, Agent, or Firm* — J.C. Patents

(57) ABSTRACT

A digital pulse oximeter with automatic orientation change function, comprising a housing that is configured to clamp a human finger being tested, a display window disposed at outside of and atop the housing, a circuit being disposed within the housing for calculating and analyzing the tested signals, and displaying them in the display window atop the housing via a display, wherein the said circuit has only one control key disposed on the housing, the said circuit allowing the display contents of the display to be always oriented properly for easy reading by connecting with one two-axis or three-axis accelerometer. The digital pulse oximeter of the present invention is featured with small size and convenient operation and can shift from one function to another using only one control key in conjunction with the interface display, thereby increasing the functions of small-sized pulse oximeters. The present invention uses accelerometers to judge the placing location of the apparatus without the need for any operation from the user, and the apparatus can automatically change the display orientation of the display, thus providing great convenience to the user.

6 Claims, 2 Drawing Sheets

DIGITAL PULSE OXIMETER WITH AUTOMATIC DIRECTION-CHANGING FUNCTION

FIELD OF THE INVENTION

The invention relates to a medical device, and more particularly, to a digital pulse oximeter with automatic orientation change function. The pulse oximeter is small in size and convenient to operate and can automatically change the display orientation of the display and measure PI value.

DESCRIPTION OF THE RELATED ARTS

A pulse oximeter is a non-invasive medical device for continuously monitoring the blood oxygen saturation of arteries in a human body. As a common device of anesthesia monitoring and intensive care in hospitals, the device has also been widely used in a variety of mobile cares and sleep cares at places other than hospitals. The development of both family and community medical healthcare systems has put forward new requirements on the design and manufacturing of pulse oximeters, in particular, it is highly desirable that wearable pulse oximeters that are characterized by low price yet high performance and are widely adaptable to families and medical treatment network at community level be provided.

Perfusion Index (PI) is a measure of the pulsatile blood flow of an examinee, namely, the perfusion capability of a human body. As the blood oxygen saturation is measured, the body tissues giving rise to light attenuation involve the blood ingredients (arterial blood and venous blood) and non-blood ingredients (skin, bone and connective tissue). The non-blood ingredients do not change with the pulsatile process, while the blood ingredients vary with the pulse-induced changes in blood flow into and out of the vascular beds. Therefore, the light absorption of the former (non-blood ingredients) is constant (called as direct current), while the light absorption of pulsatile blood flow ingredients is pulsatile (called as alternating current). The PI value can be derived by arithmetically adjusting the ratio of alternating current component to direct current component. The larger the pulsatile blood flow, the larger the pulsatile component, and hence the higher the PI value is. Therefore, both the tested parts (skin, nail, and bone etc.) and the perfusion of the examinee (flow of arterial blood) will influence the PI value. As the sympathetic nerves affect the heart rate and arterial blood pressure (consequently, influence the arterial blood flow), the neuromodulation system or mental status of a human being will influence the PI value indirectly. As a result, the PI value varies from one anaesthetic state to another.

Today, the pulse oximeters commercially available in the domestic and overseas markets generally fall into two categories—analog type and digital type. Analog oximeters have a complex circuitry which places high requirements on parameter matching between various analog channels. This has greatly limited the oximeter performance and lead to a high price. In contrast, digital oximeters can eliminate the defects of analog oximeters and have been widely used. The pulse oximeters currently available in the market have multiple keys, are large in size and complex to operate. Most of the pulse oximeters are only provided with the functions of measuring blood oxygen saturation and pulse rate. In addition, they have the display interface orientation changed manually and are limited in function and are not convenient to operate.

SUMMARY OF THE INVENTION

The objective of this invention is to provide a digital pulse oximeter with automatic orientation change function. The digital pulse oximeter of present invention is small in size and convenient to operate and allows automatic change of display orientation of a display and measurement of PI value.

The objective of the present invention is achieved through the technical schemes as described below: a digital pulse oximeter with automatic orientation change function, comprising a housing that is configured to clamp a human finger being tested, a display window disposed at outside of and atop the housing, a circuit being disposed within the housing for calculating and analyzing the tested signals, and displaying them in the display window atop the housing, wherein the said circuit has only one control key on the housing, the said circuit allowing the display contents to be always oriented properly for easy reading by connecting with one two-axis or three-axis accelerometer.

The said housing consists of an upper housing body and a lower housing body. The upper housing body and the lower housing body are disposed such that they are stacked together. One end of both the upper and lower housing body is the measurement end where a finger is placed. A pivot and a reset spring disposed between the upper housing body and the lower housing body enable them to be opened and closed at the measurement end.

The said circuit comprises a light-frequency converter, a red infrared light emitting diode, a light-emitting driving circuit, a microprocessor module, a display and a power supply module; the said power supply module supplies power to the light-frequency converter, the red infrared light emitting diode, the light-emitting driving circuit, the microprocessor module, and the display; the said light-frequency converter transmits the received signals that are emitted by the red infrared light emitting diode and pass through a finger to the microprocessor module; the microprocessor module is provided with two input ends which are respectively connected with the said three-axis accelerometer and the control key.

The information displayed by the said display includes: blood oxygen saturation, pulse rate, PI value, waveform, and bar graph. The display modes of the display include: large digital display, small digital display and simultaneous display of both waveform and digital.

The said power supply module comprises a power supply and a power supply switching control circuit. The signals of the control key are connected to both the microprocessor module and the power supply switching control circuit. The said microprocessor module has a power supply turn-on holding signal that is connected to the power supply switching control circuit. When the control key is pressed down, the power supply switching control circuit acts and connects the power supply to the light-frequency converter, the red infrared light emitting diode, the light emitting driving circuit, the microprocessor module and the display. The power supply turn-on holding signal of the microprocessor module, based on the time of press-down of the control key, decides whether the power supply switching control circuit is continuously turned on or turned off.

The said microprocessor module judges the orientation of the pulse oximeter based on the acceleration data of the two-axis or three-axis accelerometer, and then automatically adjusts the display orientation of the display correspondingly.

With a control table containing the press-down time of the control key established in the microprocessor module, it compares the press-down time of the control key with the control table, and then shifts from one processing function to another.

The digital pulse oximeter of the present invention is featured with simple structure, small size and convenient operation and shifts from one function to another using only one control key in conjunction with the interface display, thereby increasing the functions of a small-sized pulse oximeter. The present invention uses accelerometers to judge the placing location of the device without the need for any operation from the user, and the device can automatically change the display orientation of the display, thus providing great convenience to the user.

BRIEF DESCRIPTION OF THE DRAWINGS

The above features and advantages, and other features and advantages, of the present invention are readily apparent from the following detailed description of the best modes for carrying out the invention when taken in connection with the accompanying drawings wherein.

DESCRIPTION OF THE PREFERRED EMBODIMENT

Figure 1:
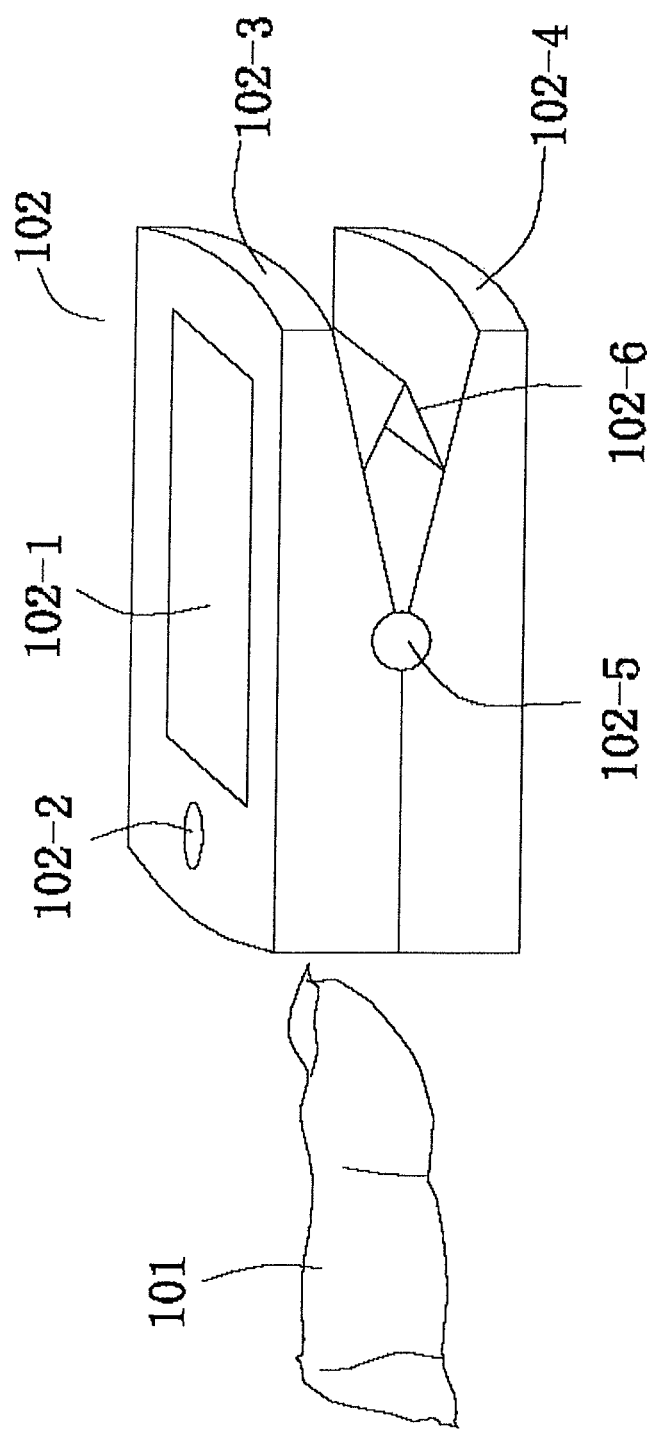
FIG. 1 is a schematic view of this invention
Figure 2:
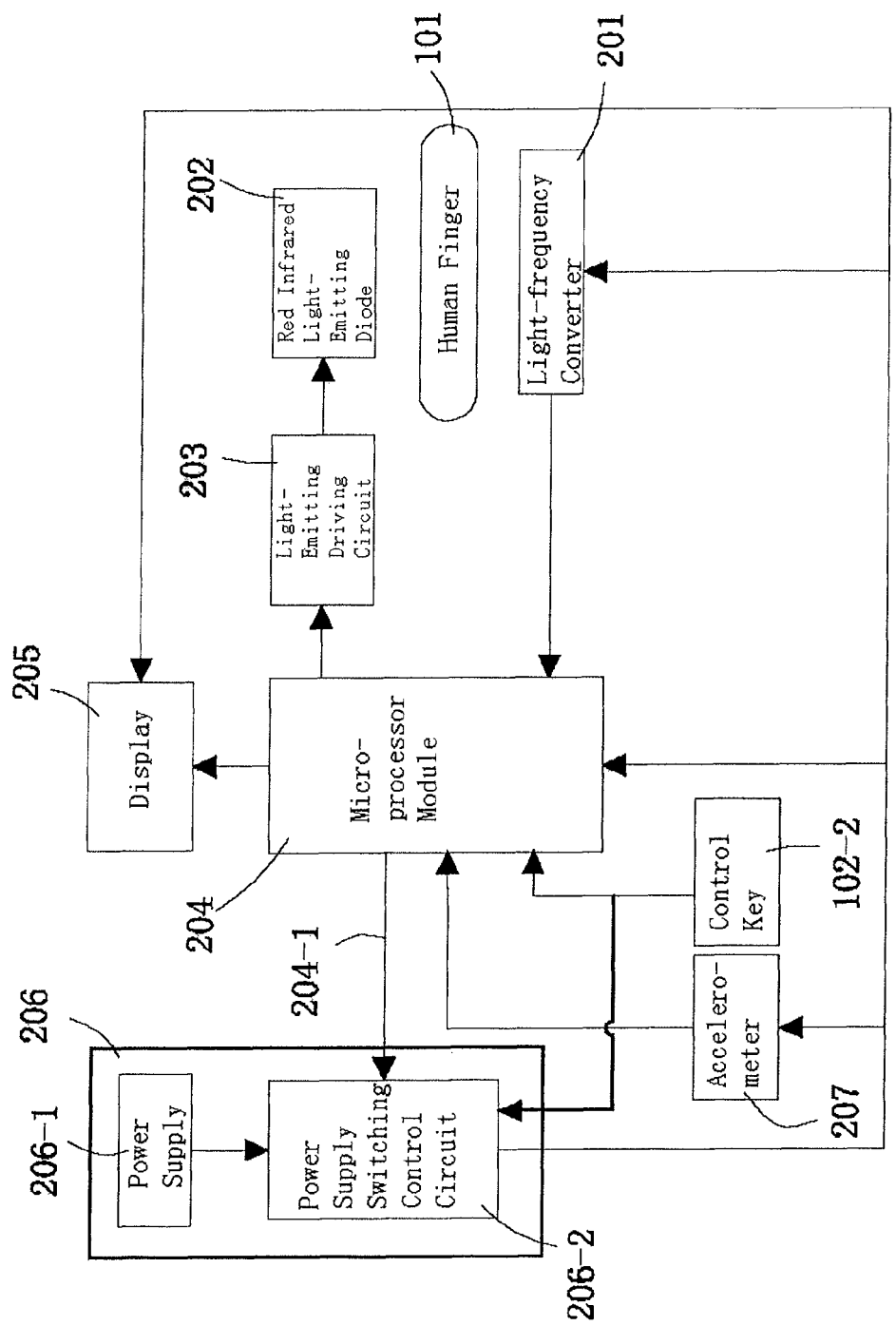
FIG. 2 is a schematic diagram of the circuit of this invention

Referring to FIGS. 1 and 2, a digital pulse oximeter with automatic orientation change function is illustrated therein. The digital pulse oximeter comprises a housing 102 that is configured to clamp a human finger 101 being tested, a display window 102-1 disposed at outside of and atop the housing, a circuit being disposed within the housing for calculating and analyzing the tested signals, and displaying them in the display window atop the housing, wherein the said circuit has only one control key 102-2 on the housing, the said circuit allowing the display contents to be always oriented properly for easy reading by connecting with one two-axis or three-axis accelerometer.

As shown in FIG. 1, the said housing consists of an upper housing body 102-3 and a lower housing body 102-4. The upper housing body and the lower housing body are disposed such that they are stacked together. One end of both the upper and lower housing body is the measurement end where a finger is placed. A pivot 102-5 and a reset spring 102-6 that are disposed between the upper housing body and the lower housing body enable them to be opened and closed at the measurement end.

As shown in FIG. 2, the circuit in this embodiment comprises a light-frequency converter 201, an infrared light emitting diode 202, a light-emitting driving circuit 203, a microprocessor module 204, a display 205 and a power supply module 206; the said power supply module supplies power to the light-frequency converter, the infrared light emitting diode, the light-emitting driving circuit, the microprocessor module and the display; the said light-frequency converter transmits the received signals that are emitted by the red infrared light emitting diode and pass through a finger to the microprocessor module; the microprocessor module is provided with two input ends which are respectively connected with the said three-axis accelerometer 207 and the control key 102-2.

In this embodiment, the information displayed by the display includes blood oxygen saturation, pulse rate, PI value, waveform, and bar graph. The display modes of the display include large digital display, small digital display and simultaneous display of both waveform and digital.

In this embodiment, the said power supply module comprises a power supply 206-1 and a power supply switching control circuit 206-2. The signals of the control key are connected to both the microprocessor module and the power supply switching control circuit. The said microprocessor module has a power supply turn-on holding signal 204-1 that is connected to the power supply switching control circuit. When the control key is pressed down, the power supply switching control circuit acts and connects the power supply to the light-frequency converter, the red infrared light emitting diodes, the light emitting driving circuit, the microprocessor module and the display. The power supply turn-on holding signal of the microprocessor module, based on the time of press-down of the control key, decides whether the power supply switching control circuit is continuously turned on or turned off.

Meanwhile, with a control table containing the press-down time of the control key established in the microprocessor module according to the embodiment, it compares the press-down time of the control key with the control table, and then shifts from one processing function to another.

The detailed work steps in accordance with this embodiment are as follows:

First, a control table containing the press-down time of the control key is established in the microprocessor module.

Step 1: press the control key, the power supply switching control circuit conducts and the microprocessor module is powered on to reset; then, the microprocessor module is initialized and tests the press-down time of the control key; if the press-down time of the control key is long, the microprocessor module outputs a power supply turn-on holding signal to hold the power supply switching control circuit on and the system is powered on; if the press-down time of the control key is short, the microprocessor module halts the power supply turn-on holding signal to power off the power supply switching control circuit and the system is powered off;

When the system is powered on:

Step 2: the display displays a main interface, and then the microprocessor module processes the data to obtain the blood oxygen data which is displayed; the microprocessor module controls a loudspeaker module to decide if an alarm is issued and awaits a key operation;

Step 3: if a press-down signal is input, the microprocessor module judges whether it is a long press-down or a short press-down; if it is a long press-down, the microprocessor module enters the menu; if it is a short press-down, the microprocessor module judges the alarming status then; if a alarm occurs, an alarming pause operation is performed; if an alarming pause operation occurs or no alarm is issued, the display mode of the interface is changed.

Step 4: if the display stays at the main interface, the system returns to execute Step 3; if an operating interface displays, the execution will continue;

Step 5: if a press-down operation occurs, the microprocessor module judges whether it is a long press-down or a short press-down; if it is a short press-down, the system performs the "jump to next step" operation; if it is a long press-down, the system executes "confirm" operation.

Step 6: the system determines whether a "jump to next step" operation or a "confirm" operation is executed according to the interface and location of the display bar or cursor.

Step 7: steps 4, 5, and 6 are executed until the device is turned off.

The operating principle of the said oximeter is as follows: the said microprocessor module chronologically outputs two pulse signals periodically, and drives the light-emitting diode to emit red and infrared light via the light-emitting drive circuit. The emitted light pulses pass through a human tissue (namely, a finger) and are attenuated and modulated before being received by the light-frequency converter where they are converted into a pulse train whose frequency is linearly proportional to the pulsed light. Such pulse train is transmitted to the I/O interface of the microprocessor module which then adjusts the light intensity based on the results and calculates the blood oxygen saturation and pulse frequency rate. In the calculation of blood oxygen saturation, the PI value, namely, the perfusion index, is obtained by dividing the direct current component with the alternating current component. The blood oxygen saturation, pulse rate value and PI value are ultimately displayed on the display.

This embodiment involves the use of a highly sensitive three-axis accelerometer which can read the low-gravity fall, incline, movement, placement, shake, and swing respectively along the orientations of X, Y, and Z axis with a extremely high sensitivity. The accelerometer transmits the measured data to the microprocessor module which, based on the data of fall, incline, movement, placement, shake, and swing along the orientations of X, Y, and Z axis, judges the orientation of the pulse oximeter and then automatically adjusts the display orientation of the display.

With the additional function of automatically changing the display orientation of the display, the digital pulse oximeter of the present invention permits convenient change of the display orientation of the display without any operation made by the users, thus achieving convenient and easy use thereof.

People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A digital pulse oximeter with automatic orientation change function, comprising a housing that is configured to clamp a human finger being tested, a display window disposed at outside of and atop the housing, a circuit being disposed within the housing for calculating and analyzing tested signals, and displaying them in the display window atop the housing via a display, wherein the circuit has only one control key disposed on the housing and the circuit is connected with a two-axis accelerometer or three-axis accelerometer to control display contents of a display in the display window to be always oriented properly for easy reading;

wherein the circuit comprises a light-frequency converter, a red infrared light emitting diode, a light-emitting driving circuit, a microprocessor module, the display and a power supply module, the power supply module supplies power to the light-frequency converter, the red infrared light emitting diode, the light-emitting driving circuit, the microprocessor module, and the display; the light-frequency converter transmits a received signal that is emitted by the red infrared light emitting diode and passes through a finger to the microprocessor module; the microprocessor module is provided with two input ends which are respectively connected with the two-axis accelerometer or three-axis accelerometer and the control key;

wherein the microprocessor module has a control table containing a long press-down time and a short press-down time of the control key, and the microprocessor module is configured such that when the control key is pressed, the microprocessor module tests the press-down time of the control key and shifts from one processing function to another according to the length of the press-down time of the control key and the control table.

2. The digital pulse oximeter with automatic orientation change function as claimed in claim 1, wherein the housing comprises an upper housing body and a lower housing body, the upper housing body and the lower housing body being disposed such that they are stacked together, one end of both the upper housing body and the lower housing body being a measurement end where a finger is placed, a pivot and a reset spring disposed between the upper housing body and the lower housing body enabling them to be opened and closed at the measurement end.

3. The digital pulse oximeter with automatic orientation change function as claimed in claim 1, wherein the information displayed by the display includes blood oxygen saturation, pulse rate, PI value, waveform, and bar graph; the display modes of the display include large digital display, small digital display and simultaneous display of both waveform and digital.

4. The digital pulse oximeter with automatic orientation change function as claimed in claim 1, wherein the power supply module comprises a power supply and the power supply switching control circuit, the signals of the control key are connected to both the microprocessor module and the power supply switching control circuit, the microprocessor module has a power supply turn-on holding signal that is connected to the power supply switching control circuit; when the control key is pressed down, the power supply switching control circuit acts and connects the power supply to the light-frequency converter, the red infrared light emitting diode, the light emitting driving circuit, the microprocessor module and the display; the power supply turn-on holding signal of the microprocessor module, based on the time of press-down of the control key, decides whether the power supply switching control circuit is continuously turned on or turned off.

5. The digital pulse oximeter with automatic orientation change function as claimed in claim 1, wherein the microprocessor module is configured to judge the orientation of the pulse oximeter based on acceleration data of the two-axis accelerometer or the three-axis accelerometer, and then automatically adjusts the display orientation of the display correspondingly.

6. The digital pulse oximeter with automatic orientation change function as claimed in claim 1, wherein the shifting from one processing function to another according to the length of the press-down time of the control key and the control table comprises:

when the control key is pressed for initiating the microprocessor module, if the press-down time of the control key is a long press-down time, the microprocessor module outputs a power supply turn-on holding signal to hold the power supply switching control circuit on and the digital pulse oximeter is powered on; if the press-down time of the control key is a short press-down time, the microprocessor module halts the power supply turn-on holding signal to power off the power supply switching control circuit and the digital pulse oximeter is powered off;

when the control key is pressed while the digital pulse oximeter is powered on, if the press-down time is a long press-down time, the microprocessor module enters a menu; if the press-down time is a short press-down time, the microprocessor module judges alarming status then; if an alarm occurs, an alarming pause operation is performed; if an alarming pause operation occurs or no alarm is issued, display mode is changed;

when the control key is pressed while an operating interface displays, if the press-down time is a short press-down time, the digital pulse oximeter performs a "jump to next step" operation; if the press-down time is a long press-down time, the digital pulse oximeter executes a "confirm" operation.

* * * * *